United States Patent
Aberg

(10) Patent No.: US 8,445,542 B2
(45) Date of Patent: May 21, 2013

(54) METHODS OF ACCELERATING MUSCLE GROWTH, DECREASING FAT DEPOSITS AND IMPROVING FEED EFFICIENCY IN LIVESTOCK ANIMALS

(71) Applicant: Bridge Pharma, Inc., Sarasota, FL (US)

(72) Inventor: A. K. Gunnar Aberg, Sarasota, FL (US)

(73) Assignee: Bridge Pharma, Inc., Sarasota, FL (US)

( * ) Notice: Subject to any disclaimer, the term of this patent is extended or adjusted under 35 U.S.C. 154(b) by 0 days.

(21) Appl. No.: 13/689,173

(22) Filed: Nov. 29, 2012

(65) Prior Publication Data

US 2013/0090295 A1    Apr. 11, 2013

Related U.S. Application Data

(63) Continuation of application No. 13/185,153, filed on Jul. 18, 2011, which is a continuation of application No. 11/942,455, filed on Nov. 19, 2007, now Pat. No. 7,985,775, which is a continuation of application No. 11/755,378, filed on May 30, 2007, now abandoned.

(60) Provisional application No. 60/809,205, filed on May 30, 2006, provisional application No. 60/923,506, filed on Apr. 13, 2007.

(51) Int. Cl.
*A61K 31/137*    (2006.01)

(52) U.S. Cl.
USPC ....................................................... 514/653

(58) Field of Classification Search
USPC ....................................................... 514/653
See application file for complete search history.

(56) References Cited

U.S. PATENT DOCUMENTS

| | | | |
|---|---|---|---|
| 4,690,951 A | 9/1987 | Anderson et al. | |
| 5,057,427 A | 10/1991 | Wald et al. | |
| 5,077,217 A | 12/1991 | Matson et al. | |
| 5,643,967 A | 7/1997 | Anderson et al. | |
| 6,372,799 B1 | 4/2002 | Aberg | |
| 6,855,334 B2 | 2/2005 | Bhatt et al. | |
| 6,974,587 B2 | 12/2005 | Trompen et al. | |
| 7,985,775 B2 | 7/2011 | Aberg | |
| 2007/0116729 A1* | 5/2007 | Palepu | 424/400 |
| 2010/0226943 A1* | 9/2010 | Brennan et al. | 424/400 |
| 2012/0015895 A1* | 1/2012 | Aberg | 514/30 |

FOREIGN PATENT DOCUMENTS

| | | |
|---|---|---|
| EP | 0 007 205 | 1/1980 |
| WO | WO 2006/064283 A1 | 6/2006 |

OTHER PUBLICATIONS

Bardsley, R.G. et al. "Effect of β-agonists on expression of calpain and calpastatin activity in skeletal muscle". Biochimie, 1992, 74:267-273.
Colbert, W.E., et al., "Beta-adrenoceptor profile of ractopamine HC1 in isolated smooth muscle and cardiac muscle tissues of rat and guinea pig", J Pharm Pharmacol, 1991, 43: 844-847.
London, C.J, et al., "Effects of a New Growth Promoter (R-albuterol) for Commercial Swine Production", Abstr. Bio2005, Philadelphia, US. Jun. 2005.
Marchant-Forde, J.N., et al., "The effects of ractopamine on the behavior and physiology of finishing pigs", J Anim Sci,. 2003, 81: 416-422.
Mills, S.E., "Biological Basis of Ractopamine Response", J. Anim. Sci., 2001, 79 (suppl1): E28-32.
Mills, S.E., et al., "Stereoselectivity of porcine β-adrenergic receptors for ractopamine stereoisomers" J. Anim. Sci., 2003, 81: 122-129.
Mills, S.E., et al., "Beta-adrenergic receptor subtypes that mediate ractopamine stimulation of lipolysis", J. Anim. Sci., 2003, 81: 662-668.
Post J., et al., "Physiological Effects of Elevated Plasma Corticosterone Concentrations in Broiler Chicken. An Alternate Means by which to Assess the Physiological Stress", Poult. Sci., 2003, 82:1313-1318.
Ricke, E.A., et al., "Effects of ractopamine HC1 stereoisomers on growth, nitrogen retention and carcass composition in rats", J. Anim, Sci., 1999. 77: 701-707.
Shappell, N.W. et al., "Response of C2C12 mouse and turkey skeletal muscle cells to the beta-adrenergic agonist ractopamine". J. Anim. Sci., 2000, 78: 699-708.
Stadler, K, "Porcine Stress Syndrome and Its Effects on Maternal, Feedlot and Carcass Quantitative and Qualitative Traits". The University of Tennessee, Agricultural Extension Service, PB 1606.
Warris, P.D., et al., "Relationship between subjective and objective assessment of stress a slaughter and meat quality in pigs", Meat Science, 1994, 38:329-340.
Watkins, L.E., et al., "The effect of various levels of ractopamine hydrochloride on the performance and carcass characteristics of finishing swine", J. Anim. Sci., 1990. 68: 3588-3595.
Williams, N.H, et al., The impact of ractopamine, energy intake and dietary fat on finisher pig growth performance and carcass merit, J. Anim. Sci., 1994, 72: 3152-3162.

* cited by examiner

*Primary Examiner* — Raymond Henley, III
(74) *Attorney, Agent, or Firm* — Viksnins Harris & Padys PLLP

(57) ABSTRACT

A method of promoting or improving the feed efficiency and the muscle to fat ratio in animals by administering to the animals a therapeutically effective amount of a pure or substantially pure RR-isomer of ractopamine is disclosed. Also disclosed are animal feed preparations and compositions and pharmaceutical preparations capable of increasing lean meat deposition in an animal or decreasing body fat, or promoting or improving the growth of an animal or improving the feed efficiency of an animal. Feed preparation, compositions and pharmaceutical preparations including therapeutically effective amounts of a pure or substantially pure RR-isomer of ractopamine are disclosed.

19 Claims, No Drawings

METHODS OF ACCELERATING MUSCLE GROWTH, DECREASING FAT DEPOSITS AND IMPROVING FEED EFFICIENCY IN LIVESTOCK ANIMALS

RELATED APPLICATIONS

This application is a continuation of U.S. application Ser. No. 13/185,153 filed Jul. 18, 2011, which is a continuation of U.S. application Ser. No. 11/942,455 filed Nov. 19, 2007, which issued as U.S. Pat. No. 7,985,755 issued Jul. 26, 2011, which is a continuation of U.S. application Ser. No. 11/755,378 filed May 30, 2007, and claims the benefit of priority of U.S. application Ser. No. 60/809,205, filed May 30, 2006 and of U.S. application Ser. No. 60/923,506, filed Apr. 13, 2007, which applications are herein incorporated by reference.

FIELD OF THE INVENTION

The invention relates to methods of increasing the muscle/fat ratio in an animal, promoting or improving the growth of an animal and/or improving the feed efficiency of animals by administering therapeutically active isomers of ractopamine or a derivative thereof to the animals in a quantity which is effective for this purpose. The invention further relates to compositions for use in the methods and to animal feed additives, which comprise one or more therapeutically active isomers of ractopamine as the active substance. The present invention refers to the use of certain adrenergic drugs in animals that have now surprisingly been found not to induce stress or the aggravation of stress in said animals.

BACKGROUND OF THE INVENTION

Adrenergic beta-agonistic drugs characteristically contain as part of their structure an ethanolamine or 2-amino-ethanol moiety. Since the chemical structures of these drugs usually comprise at least one asymmetric carbon atom, these drugs commonly exist in optically active isomeric form, with the chiral carbon atom having (R) or (S) configuration. When there is a single asymmetric carbon atom present, the beta-receptor agonists exist as individual (R) or (S) enantiomers or in racemic (RS) form, i.e. as a 50:50 mixture of (R) and (S) enantiomers.

Compounds with two chiral centers have four isomers: the RR—, SS—, RS—, and SR-isomers. Such compounds (e.g. formoterol, ractopamine) may exist in a number of forms i.e. in the pure RR or SS or RS or SR isomeric forms, or as mixtures, hereinafter called "enantiomeric pairs" of either RR/SS or RS/SR. The compound ractopamine can also exist as racemic mixtures of all four isomers (RR+SS+RS+SR) or in the form of racemic mixtures of the enantiomeric pairs (RR/SS) or (RS/SR). The isomers (RR) and (SS) are mirror images of each other and are therefore enantiomers, which have the same chemical properties and melting points. (RS) and (SR) is similarly an enantiomeric pair. The mirror images of (RR) and (SS) are not, however, super imposable on (RS) and (SR). This relationship is called diastereomerism, and (RR) is a diastereomer to (RS).

Ractopamine has the molecular formula $C_{18}H_{23}NO_3$ and racemic ractopamine is typically prepared as a hydrochloride salt. Chemically, ractopamine is differs from dobutamine in the location of only one hydroxyl group, but ractopamine is not a catecholamine and is therefore not instantaneously metabolised by catechol-O-methyl transferase. Ractopamine HCl (4-hydroxy-a-[[[3-(4-hydroxyphenyl)-1-methylpropyl]amino]methyl]benzenemethanol hydrochloride) has a molecular weight of 337.85 and a molecular formula of $C_{18}H_{23}NO_3 \cdot HCl$ (CAS number: 90274-24-1). The racemate of ractopamine is a mixture of all four isomers in approximately equal proportions.

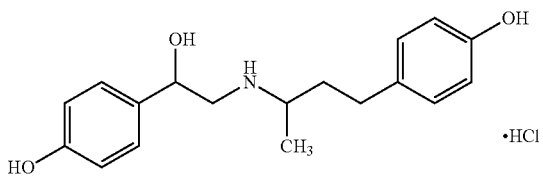 [SMILES: CC(CCc1ccc(O)cc1)NCC(O)c1ccc(O)cc1 ; Cl]

Ractopamine Hydrochloride

One form of ractopamine—the racemic mixture of all four isomers (RR/SS/RS/SR) is commercially available under the trade names PAYLEAN®, Elanco and OPTAFLEX®, Elanco and both are used as growth promotants for livestock. The RR-isomer of ractopamine is called Butopamine Hydrochloride, USAN and has extensively been tested as a cardiac stimulator for humans by Leier et al., which publications are hereby included by reference in their entirety (Thompson, M J; Huss, P; Unverferth, M D; Fasola A; Leier, C V: Hemodynamic effects of intravenous butopamine in congestive heart failure. Clin Pharmacol Ther, 1980, 28: 324-334). Butopamine was not further developed as human medication.

Although structurally identical, isomers can have different effects in biological systems: one isomer may have specific therapeutic activity while another isomer may have no therapeutic activity or may have entirely different forms of biological activity.

The pharmacological activity of beta-receptor agonists like ractopamine is to activate adrenergic beta-receptors. Activation of adrenergic beta-receptors leads to increased intracellular concentration of cyclic adenosine monophosphate (cAMP), which triggers various events in various cells and organs. Cellular responses to beta-receptor activation include for example lipolytic activity in adipose tissues, smooth muscle relaxant activity in the bronchi and increased frequency of contractions in the heart (Goodman-Gilman, The Pharmacological Basis of Therapeutics $9^{th}$ Ed., 1996 McGraw-Hill ISBN0-07-026266-7.) Most adrenergic beta-receptor agonists have affinity for two or three types of adrenergic beta-receptors. Thus, both salbutamol and ractopamine have affinity for adrenergic beta-1 and beta-2 receptors, but negligible affinity for beta-3 receptors. There is no significant effect of ractopamine on adrenergic alpha-receptors (Colbert W E, Williams P D, Williams G D: Beta-adrenoceptor profile of ractopamine HCl in isolated smooth muscle and cardiac muscle tissues of rat and guinea pig, J Pharm Pharmacol 1991, 43: 844-847.) It may therefore be concluded that ractopamine does not have direct effects on adrenergic alpha-receptors in the brain.

Of the four isomers of ractopamine, which are RR—, RS—, SR— and SS-ractopamine, it is known that RR-ractopamine is the most potent, both when tested in vitro (Mills S E, Kissel J, Bidwell C A, Smith D J, Stereoselectivity of porcine β-adrenergic receptors for ractopamine stereoisomers. J. Anim. Sci. 2003, 81: 122-129) and in vivo (Ricke E A, Smith D J, Feil V J, Larsen G L, Caton J S, Effects of ractopamine HCl stereoisomers on growth, nitrogen retention and carcass composition in rats. J. Anim, Sci. 1999, 77:701-707, which publications are hereby included in their entirety by reference.) Thus, when tested for binding affinity for porcine adrenergic β-2 receptors, RR-ractopamine was about 2.5 times as active as the racemic mixture of all four isomers (Mills et al., 2003.)

Adrenergic beta-receptor agonist drugs have pharmacological and toxicological side effects that range from minor importance to major importance. Bronchial smooth muscle relaxation by adrenergic beta-2 stimulation may be a side effect of minor importance for livestock animals. However, racemic ractopamine has been found to cause CNS-mediated stress in livestock animals (Marchant-Forde J. N., et al., The effects of ractopamine on the behaviour and physiology of finishing pigs" J Anim Sci., 2003, 81: 416-422, which publication is hereby included in its entirety by reference.) This is a side effect of major importance, as racemic ractopamine is increasing the stress levels in animals during handling and transport and is causing increased mortality during transport. Stress in livestock animals, particularly in swine, is believed to induce the PSE syndrome in the animals (poor meat quality that is pale, soft and exudative, becoming dry upon cooking).

Ractopamine, having preference for adrenergic (cardiac) $β_1$ receptors, may cause tachycardia in livestock animals by direct stimulation of cardiac $β_1$ receptors, while R-salbutamol, having preference for adrenergic $β_2$ receptors is not causing tachycardia in the livestock animals (Marchant-Forde J. N., et al., 2003 and London C. J., et al. 2005.) However, it is nevertheless not known, if the significant tachycardia in livestock animals by ractopamine is caused by CNS-mediated stress or by direct beta-receptor stimulation or both, but tachycardia is an unwanted side-effect, which may lead to cardiac tachyarrhythmias and increased lethality of livestock animals by sudden cardiac death (cardiac ventricular fibrillation.)

In many animals including livestock animals, birds and fish, stress manifests itself—directly or indirectly—in a range of forms extending from irritability to aggression. Stress may lead to cardiovascular side effects ranging from slightly elevated heart rate to serious tachycardia and cardiac arrhythmias, which in turn can lead to sudden death. The prevalence of stress-induced lethality varies among species; some having higher stress responsiveness than others (Odeh F. M., Cadd G. G., Satterlee D. G. Genetic characterization of stress responsiveness in Japanese quail. Poult Sci., 2003, 82: 31-35, which publication is hereby included in its entirety by reference.)

Stress in horses can be expressed in various ways, such as for example nervousness, anxiety and tachycardia and can be caused for example by heat, transportation and feed withdrawal. Stress in horses can also be induced by drugs or aggravated by drugs, such as for example adrenergic beta-receptor agonists that may be given to the horses of various reasons, such as for example as bronchodilators in heaves. CNS-mediated stress in horses may also lead to increased susceptibility for various diseases, such as for example allergic diseases or infectious diseases such as opportunistic bacterial infections. The use of an adrenergic beta-agonist that does not cause stress is particularly important in animals that are already suffering from stress or have a propensity for developing stress.

Stress in pigs is very common and some pigs have been shown to carry a specific stress-gene. Pigs that are homozygous to this gene are particularly stress-prone although heterozygous pigs are also more stress-prone than pigs that do not at all carry or express the stress-gene (Sterle J.: The Frequency of The Porcine Stress Gene in Texas Show Pigs. http://animalscience.tamu.edu, which publication is hereby included in its entirety by reference.) CNS-mediated stress in pigs can be expressed in various ways, such as for example aggression, tail-biting, and tachycardia and can be caused for example by heat, transportation, stocking density, human interventions, feed withdrawal, disease and aggression between males. Stress in pigs can also be caused or aggravated by drugs, such as for example racemic ractopamine (Marchant-Forde et al. 2003.) Porcine Stress Syndrome (PSS) is triggered when pigs are subjected to stress associated with transportation, restraint, fighting, mating, exercise or hot and humid weather. Pigs with PSS become dyspneic, hyperthermic, cyanotic, develop muscle rigidity and such animals often die. Some degree of stress can be observed in most pigs and most pigs may therefore have propensity for stress. The administration of certain drugs, such as racemic ractopamine to pigs may induce or aggravate PSS in swine. In addition to the well-known fact that stress induces increased mortality in swine, it has been demonstrated that stress has a negative effect on the quality of meat. Thus, the muscles from stress-positive pigs often show the PSE syndrome (pale, soft and exudative). This condition causes the carcasses to be classified as being of unacceptable or inferior quality, since the meat from such animals tend to become dry when cooked. (Stadler K: Porcine Stress Syndrome and Its Effects on Maternal, Feedlot and Carcass Quantitative and Qualitative Traits. The University of Tennessee, Agricultural Extension Service, PB 1606, which publication is hereby included in its entirety by reference.) The use of an adrenergic beta-agonist that does not cause stress is particularly important in animals that are already suffering from stress or have a propensity for developing stress.

Stress in ruminants can be expressed in various ways and in cattle ranging from anxiety to aggression or depression, increased body temperature and increased heart rate, and can be caused by a variety of factors, such as changes in environment, transportation, human contact, aggressive herd behaviour and changes in the herd social rankings, hunger, thirst, fatigue, injury or thermal extremes (Boissy, A. & Bouissou, M-F: Assessment of individual differences in behavioural reactions to heifers exposed to various fear-eliciting situations. Applied Animal Behaviour Science, 1995, 46:17-31; and Grandin, T.: Behavioural agitation during handling of cattle is persistent over time. Applied Animal Behaviour Science, 1993, 36:1-9, which publications are hereby included in their entirety by reference). The propensity for stress in cattle seems to affect most animals and the administration of drugs, such as racemic ractopamine may induce or worsen CNS-mediated stress in cattle and particularly in cattle that are predisposed for stress. Stress in cattle is a serious condition and may lead to decreased quality of the meat and increased lethality among the animals. The use of an adrenergic beta-agonist that does not cause stress is particularly important in animals that are already suffering from stress or have a propensity for developing stress.

As other examples of ruminants, sheep also develop symptoms of CNS-mediated stress due to the same or similar factors as described above for other species and may include but are not limited to changes in the environment, transportation, human contact, aggressive herd behaviour, hunger, thirst, fatigue, injury or thermal extremes. The symptoms of CNS-mediated (psychological) stress are similar to those of other species and include anxiety, aggression, increased body temperature or increased heart rate. The consequences of stress are similar to those described above for other species and include risk for decreased quality of meat and sudden death of the animals. The administration of drugs, such as racemic ractopamine may induce stress in sheep—particularly in predisposed animals or increase the symptoms of stress in said species. Stress in sheep can be a serious condition and may lead to decreased quality of the meat and increased lethality among the animals. The use of an adrenergic beta-agonist that does not cause stress is particularly important in animals that are already suffering from stress or have a propensity for developing stress.

As still another example, birds such as chickens ducks, geese, turkeys, ostriches, emus or quails may also develop CNS-mediated stress by doses of racemic ractopamine, corresponding to those necessary for obtaining increased muscle weight, decreased fat deposits and improved feed efficiency. Particularly, chickens in "grower houses" are suffering from stress or are predisposed to stress because of the high stocking density (up to 20,000 birds in a very confined space). Symptoms of stress in birds, such as for example chickens, ducks, geese, turkeys, ostriches, emus and quails, can be expressed in various ways, as for example, anxiety, aggression, increased body temperature, tachycardia and lethality and can be caused for example by heat, transportation, high stocking density, sudden environmental factors, feed withdrawal, injury or disease. The administration of the beta-receptor agonist racemic ractopamine may induce or increase stress in birds. CNS-mediated stress in birds—and particularly in chicken—may lead to decreased quality of the meat and increased lethality among the animals.

Stress may also manifest itself in farmed fish, such as for example barramundi, carp, cod, perch, salmon, trout and tilapia. Symptoms of stress and symptoms for predisposition (propensity) for stress in farmed fish can be observed as increased activity as for example during feeding frenzy and stress can lead to sudden death of the fish. Stress in fish can be caused for example by extreme temperatures, environmental factors, disease, parasites, handling or transportation. The administration of exogenous beta-receptor agonists may lead to stress in animals that are predisposed for developing stress or may cause a worsening of the symptoms of stress in fish, leading to decreased quality of the meat and increased lethality among the animals. The use of an adrenergic beta-agonist that does not cause stress is particularly important in animals that are already suffering from stress or have a propensity for developing stress.

Stress in animals can be monitored, judged and rated by individuals who are skilled in the art of animal psychology. In addition to monitoring and rating the behaviour of the animals, objective parameters are being used, such as for example determination of the concentration of circulating corticosteroid levels and heterophil counts. (Post J, Rebel J M J, ter Huurne A A: Physiological Effects of Elevated Plasma Corticosterone Concentrations in Broiler Chicken; An Alternate Means by which to Assess the Physiological Stress. Poultry Science, 2003, 82: 1313-1318, which publication is hereby included in its entirety by reference.) Depending on the species, stress in animals in response to exogenous adrenergic stimulation can also be monitored by parameters such as body temperature, heart rate, spontaneous motility, aggression, ease of handling and even weight loss (Marchant-Forde J. N. et al, 2003.)

The use of an adrenergic beta-agonist that does not cause stress is particularly important in animals that are already suffering from stress or have a propensity for developing stress. The use of an adrenergic beta-agonist that does not cause stress is particularly important in animals that are already suffering from stress or have a propensity for developing stress. As mentioned above, predisposition of stress in livestock animals is common and it will be advantageous to avoid the worsening of the stress in these animals that is induced by racemic ractopamine.

SUMMARY OF THE INVENTION

It has now surprisingly been found that parameters, such as for example the amount of adipose tissue ("fat") in an animal, the amount of muscle tissue ("lean meat") in an animal, growth of an animal, the feeding efficiency of an animal, and the muscle-to-fat ratio of an animal can be greatly improved by administering pure or substantially pure RR-isomer of ractopamine, a pharmaceutically acceptable salt, solvate or polymorph thereof, while side effects such as aggressiveness and other symptoms of stress that can be observed in animals given a formulation containing racemic ractopamine can be avoided or substantially avoided. Thus, the applicant has found that by administering a therapeutically effective amount of the pure or substantially pure RR-isomer of ractopamine, a pharmaceutically acceptable salt, solvate or polymorph thereof, the beneficial effects of racemic ractopamine as a growth promoter for livestock are maintained or improved, while side effects such as aggressiveness and other symptoms of stress that can be observed in animals given a formulation containing racemic ractopamine can be avoided or substantially avoided. The term "substantially avoided" indicates the side effects are minimized, when administering the pure or substantially pure RR-isomer of ractopamine, a pharmaceutically acceptable salt, solvate or polymorph thereof at dosage rates at which racemic ractopamine is customarily administered. Of course, very high doses—such as doses used during toxicology testing—may still induce the side effect.

The pharmacological explanation(s) for this surprising finding is/are unknown, but a major drawback with ractopamine administration is the drug-induced stress with concomitant negative effects on the quality of the meat as well as the increased mortality among animals treated with racemic ractopamine, can now be completely or substantially avoided.

Accordingly, the invention provides a method of promoting or improving the growth of an animal by administering to the animal an effective amount of pure or substantially pure RR isomer of ractopamine.

In particular, the present invention provides a method of promoting muscle growth, decreasing fat deposits or improving feed efficiency of animals, which comprises administering to said animal an effective amount of the pure or substantially pure RR-enantiomer of ractopamine.

In one embodiment, the present invention provides a method of promoting muscle growth of an animal by administering to the animal an effective amount of the pure or substantially pure RR-isomer of ractopamine.

In another embodiment, the present invention provides a method of improving the feed efficiency of an animal by administering to the animal an effective amount of thepure or substantially pure RR-isomer of ractopamine.

In another embodiment the invention provides a method of improving the muscle to fat ratio in an animal by administering to the animal an effective amount of thepure or substantially pure RR-isomer of ractopamine.

Furthermore, it has surprisingly been found that the tissue residues of total ractopamine are lower when RR-ractopamine is being used as a growth promoter for livestock than when a racemic mixture of ractopamine is being used. Thus, in another embodiment the invention provides a method for decreasing tissue residues of ractopamine by administering to the animal a therapeutically effective amount of a ractopamine formulation that contains a pure or substantially pure RR-isomer of ractopamine. Thus humans eating the meat from livestock animals treated with RR-ractopamine, rather than racemic ractopamine, will be exposed to decreased amounts of total ractopamine. The term "total ractopamine" as used herein refers to the sum of all ractopamine isomers, enantiomeric pair, and metabolites thereof. The scientific explanation for the low tissue residues of total ractopamine in animals given RR-ractopamine is not known, but it can be speculated that lower doses and an accelerated metabolism of RR-ractopamine, which has now surprisingly been found, may contribute to the favorably low tissue residues after administration of RR-ractopamine to livestock animals.

In another embodiment the invention provides a method of treating horses suffering from heaves by administering to these horses an effective amount of the pure or substantially pure RR-isomer of ractopamine. Using RR-ractopamine for horses suffering from heaves induces effective bronchorelaxation. The therapeutic goals will be achieved without causing or worsening drug-induced CNS-mediated stress in these animals that often are significantly predisposed to stress because of their breathing difficulties.

In another embodiment the invention provides a protein-containing feed formulation including the pure or substantially pure RR-stereoisomer of ractopamine. The feed formulation is capable of increasing lean meat deposition in an animal and/or of improving the lean meat/fat ratio in an animal and/or promoting or improving the growth of an animal or improving the feed efficiency of an animal. The formulation contains a sufficient amount of a protein-containing animal feed mixed with the pure or substantially pure RR-stereoisomer of ractopamine to provide from about 1 to 500 ppm of RR-ractopamine in the feed. The concentration of crude protein and minerals in feed for various livestock animal species are well known to those skilled in the art and will meet or exceed the limits suggested by the National Research Council (1990.)

In still another embodiment the invention provides compositions and pharmaceutical formulations for use in the above methods, which include a therapeutically effective amount of the pure or substantially pure RR-stereoisomer of ractopamine.

The use of the present invention will also facilitate the handling of animals, in particular livestock animals, birds, farmed fish and farmed crustaceans, since animals treated with racemic ractopamine are frequently demonstrating symptoms of stress and are therefore more difficult to handle than animals treated with pure or substantially pure RR-ractopamine (Marchant-Forde et al. 2003.)

According to the present invention there are also advantages of administering to animals an enantiomeric mixture consisting of approximately 50% RR-ractopamine and approximately 50% SS-ractopamine, or a eutectic mixture since such RR/SS enantiomeric mixtures have surprisingly been found to offer the same advantages as racemic mixtures containing all four isomers of ractopamine, but said mixtures of RR— and SS-ractopamine are having a lesser propensity for causing stress and stress-related side effects than a racemic mixture containing all four isomers of ractopamine. The risk for racemization of the RR-isomer is eliminated or significantly decreased when a mixture containing RR+SS enantiomers, rather than a single isomer, is used.

There are also advantages of administering to livestock animals an enantiomeric mixture consisting of approximately 50% RS-ractopamine and approximately 50% SR-ractopamine, or a eutectic mixture since such RS/SR enantiomeric mixtures have now been found to offer the same advantages as racemic (RR—, RS—, SR—, and SS) ractopamine. These RS/SR enantiomeric pairs have now been found to offer the same advantages as a racemic mixture containing all four isomers of ractopamine, but said mixtures of RS— and SR-ractopamine have a lesser propensity for causing side effects than a racemic mixture containing all four isomers of ractopamine. The risk for racemization is significantly decreased when a mixture containing RS+SR enantiomers, rather than a single isomer, is used.

DISCLOSURE OF THE INVENTION

General

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features. Each document, reference, patent application or patent cited in this text is expressly incorporated herein in its entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by the specific embodiments described herein, which are intended for the purpose of exemplification only. Functionally equivalent products, formulations and methods are clearly within the scope of the invention as described herein.

The invention described herein may include one or more ranges of values (e.g. dose, concentration, etc). A range of values will be understood to include all values within the range, including the values defining the range, and values adjacent to the range, which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers.

It is also noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

The term "animal" includes any animals that are bred for human food, in particular livestock, or farm animals such as, ruminants (such as for example cattle and sheep), horses, swine, and deer, birds (such as for example chickens, turkeys, ducks, quails and geese), and farmed fish and farmed crustaceans.

The term "ractopamine" in this document refers to the free amine or to a salt or solvates of ractopamine.

Terms like "pure RR-ractopamine", "pure RR-isomer of ractopamine" and the like, refer to ractopamine having an optical purity of RR-ractopamine that is 98% by weight or better, which means the RR-isomer is present at a concentration of 98% by weight or more, while the total concentration (i.e. the sum) of the corresponding RS—, SR— and SS-isomers is 2% by weight or less, based on the total amount of ractopamine present.

The terms "substantially pure RR-ractopamine", "substantially pure RR-isomer of ractopamine" and the like, refer to an optical purity of RR-ractopamine that is 80% by weight or better which means a concentration of 80% weight or more of RR-ractopamine and 20% by weight or less of the sum of the corresponding RS—, SR— and SS-isomers, based on the total amount of ractopamine present. In a more preferred embodiment, a "substantially pure RR-ractopamine" contains 90% by weight or more of RR-ractopamine and 10% or less of the sum of the RS and SR and SS-isomers of ractopamine.

The terms "stress" and "CNS-mediated stress" are used as synonyms herein and refer to CNS-mediated (psychological) stress (as opposed to exercised-induced stress) with consequences leading to the expression of psychological symptoms such as for example aggressiveness, and/or other symptoms such as changes in body temperature, changes in the concentrations of circulating corticosteroids, increased heart rate, increased mortality and decreased quality of meat products.

The term "growth promoter" as used herein, refers to a chemical entity that upon administration to livestock animals will have a favourable effect on feed efficiency and on the muscle-to-fat ratio in the carcass of said livestock animals.

The term "feed efficiency" as used herein, refers to the relationship between feed intake and weight gain in livestock animals. Improved feed efficiency means that the ratio feed intake/weight gain is decreased.

The term "muscle-to-fat ratio" as used herein, refers to the total weight of body fat, divided with the total weight of muscle (meat). The compounds of the present invention cause a decrease in total body fat and an increase in muscle weight, as described in more detail elsewhere in this document.

Other definitions for selected terms used herein will be found within the description of the invention and apply throughout. Unless otherwise defined, all other scientific and technical terms used herein have the same meaning as commonly understood by individuals who are skilled in the art to which the invention belongs.

DETAILED DISCLOSURE OF THE INVENTION

In case certain salt-forms of pure or substantially pure isomers of ractopamine have a propensity of racemization, other salt forms or the free amine form of said compound may have a significantly lower propensity for racemization or can be considered as being optically stable.

The present invention relates to method of administering to animals a therapeutically effective amount of the pure or substantially pure RR-isomer of ractopamine rather than racemic ractopamine, whereby a decrease in body fat deposits, increase in muscle mass and improvement of feed efficiency are obtained, while alleviating the concomitant liability of certain adverse side effects associated with the administration of a ractopamine racemate. In addition, a promotion or improvement of growth (increased weight gain) is obtained in most species.

The present invention also relates to a method of decreasing residues of ractopamine in the carcasses of animals. To this end, it has now been found that by administering to animals a therapeutically effective amount of pure or substantially pure RR-stereoisomer of ractopamine or of a ractopamine formulation containing the pure or substantially pure RR-stereoisomer of ractopamine rather than racemic ractopamine, a decrease of residual concentration of ractopamine in the carcass is obtained.

It is understood by those skilled in the art that increased body weight occurs when the increase in muscle weight exceeds the loss in weight caused by the loss of fat tissue.

The term "ractopamine" as used herein refers not only to the free base, but also refers to acid addition salts or solvates thereof. Acid addition salts include, for example addition salts of ractopamine prepared with various acids, for example, hydrochloric acid, hydrobromic acid, sulphuric acid, phosphoric acid, nitric acid, or organic acids, such as citric acid, fumaric acid, tartaric acid, acetic acid, maleic acid, benzoic acid, p-toluenesulphonic acid, methanesulphonic acid, and the like. Hydrate forms and polymorphs are also included in the present invention; particularly forms that can be manufactured as dry powder or forms that are water-soluble. Reference is made to Merck Index 11th edition (1989) items 9089, 209, 3927, 4628, 8223, 5053, 5836, 8142, 2347, 7765, 1840, 9720, 7461, 1317,4159, and 963 and references cited therein and, for Am. Rev. Resp. Dis. 1988, 137: (4; 2/2) 32, the disclosures of which are herein incorporated in their entirety by reference. Importantly, the free amine form of pure, or substantially pure RR-ractopamine, has now been found to be optically stable.

Like other adrenergic beta-receptor agonists (WO 2006/064283 A1), racemic forms of ractopamine, enantiomeric pairs of ractopamine and single isomers of ractopamine, such as for example RR-ractopamine, are expected to have various polymorphs that may have favourable crystalline structure and/or favourable chiral stability and/or favourable biological effects. All such polymorphs are hereby encompassed in the present invention.

Long-term stability testing of RR-ractopamine has not been concluded and it is possible that the free amine or some of the salt form(s) may be more optically and/or chemically stable than the hydrochloride salt. The free amine has the chemical name RR-4-hydroxy-a-[[[3-(4-hydroxyphenyl)-1-methylpropyl]amino]methyl]benzenemethanol. RR-ractopamine hydrochloride has the chemical name RR-4-hydroxy-a-[[[3-(4-hydroxyphenyl)-1-methylpropyl]amino]methyl] benzene methanol HCl; melting point 176-176.5°; optical rotation $[alpha]_D$-22.7°; $[alpha]_{365}$-71.2° (c=3.7 mg/ml in methanol) (Merck Index, 1996, 12: 1392-1393).

As used herein, the terms "therapeutically effective amount" or "effective amount" or the like refer to an amount of compound, such as for example an adrenergic receptor agonist or an antibacterial compound that is sufficient to obtain a sufficient beneficial effect. In the present context and with regard to animals, a sufficient beneficial effect is considered to be present, if one or more of the aforementioned effects are achieved. In particular, a sufficient beneficial effect is considered to be present, if the treatment offers a financial return of at least the cost of the treatment, more preferably at least three times the cost of the treatment. The financial returns of the treatment may vary among animal species and will depend on factors like decreased mortality, decreased morbidity, improved meat quality, cost of treatment, improved lean/fat pricing bonus, etc. As will be realized by those skilled in the art, the amount of RR-ractopamine constituting such an amount of drug will depend on the animal species, the duration of the treatment and numerous other factors.

The administration of racemic ractopamine is known to induce stress in animals and can also cause worsening of existing stress in said animals. The methods of the present invention are particularly useful for treating animals with a growth promoter, a repartitioning agent, etc., if said animals already suffer from stress that is induced by their environment or by other factors, since drug-induced stress by adrenergic beta-receptor agonists, such as racemic (RR/SS+RS/SR) ractopamine may significantly add to, potentiate, or make worse stress in the animals.

RR-ractopamine is a growth promoter and a repartitioning agent for use in livestock or other animals. Although, RR-ractopamine is not likely to cure stress, treatment of animals with the repartitioning agent RR-ractopamine has surprisingly been found not to worsen existing stress or induce stress in animals and particularly not in animals that are predisposed or prone to stress.

Preferably the RR-isomer of ractopamine will be used in the method of the invention, where said method is used to treat animals that are prone to stress. The use of the pure or substantially pure form of the single isomer RR-ractopamine will eliminate or substantially reduce drug-induced toxic effects and drug-induced pharmacological side effects that reside in the RS—, SR— or SS-isomers of ractopamine. The use of the pure single isomeric form of RR-ractopamine will completely eliminate all drug-induced toxic effects that exclusively reside in the RS—, SR or SS-isomer of ractopamine.

The use of a single RR-isomer of ractopamine, rather than the racemic form of ractopamine, as a growth promoter in livestock animals will decrease the tissue drug residues of total ractopamine in the edible parts of livestock animal bodies since RR-ractopamine has now been found to be more potent as a beta-receptor agonist than racemic forms enantiomeric pairs or any other single isomer of ractopamine and can therefore be used in lower doses than any other form of ractopamine. The use of the RR-isomer by itself will eliminate drug residues of the other isomers. The use of the single RR-isomer rather than a racemic mixture may also have advantages at the sites of metabolism and at the receptor sites, since drug interactions and receptor down-regulation by the other isomers can be avoided when a single isomer is used. The reason for the very potent lipolytic activity of the RR-isomer of ractopamine is not known, but may be due to effects on various types of adrenergic receptors.

It is well known by farmers who are using the commercially available form of ractopamine for livestock animals that this form of ractopamine is causing stress in livestock animals (Marchant-Forde J. N., et. al. 2003). It has now been found that RR-ractopamine does not cause this side effect when used in doses that correspond to regular doses of racemic ractopamine in livestock animals. Stress is a significant side effect of racemic ractopamine and causes increased heart rate and increased mortality in animals, particularly during handling and transport, as well as induction of the PSE syndrome (poor meat quality that is pale, soft and exudative) in swine. It is considered to be a major improvement of growth promoter therapy that the use of RR-ractopamine, rather than racemic ractopamine will avoid the induction of stress or the worsening of stress when used in doses suitable for growth promotion in livestock animals.

Preferential selection of the RR isomer also offers beneficial advantages since pro-inflammatory effects of the distomers, i.e. SS—, SR— and RS-isomer, and smooth muscle hyperreactivity by distomeric molecules will be avoided. Such side effects by the distomers may be exacerbated due to the pharmacokinetic properties (slow metabolism) of said distomeric forms of ractopamine. The avoidance of these side effects is of particular importance when RR-ractopamine is used as medication for horses, suffering from heaves.

Preferential selection of the RR isomer also offers beneficial cardiac effects as this form of ractopamine has not revealed detrimental effects on cardiovascular parameters in animals at concentrations that correspond to the doses, which are suitable for growth promotion, which means doses of RR-ractopamine that decrease body fat, increase muscle mass, improve feed efficiency or increase body weight of animals. Thus, RR-ractopamine may be used while avoiding the induction or worsening of stress in livestock animals, for improving the quality of the carcass and the feed efficiency. The term "improving the quality of the carcass" as used in this document implies an increase in lean muscle weight, decrease in fat content, increase of the lean/fat ratio and avoidance of impaired meat quality, such as for example dry meat, discolored meat and PSE syndrome meat.

The methods of the present invention have advantages also for the companion animal owner or the veterinarian who wishes to increase leanness and trim unwanted fat from obese companion animals, since the present invention provides the means by which this can be accomplished.

For the farmers, the method of the present invention yields leaner animals, which command higher prices from the meat industry. It was also noted that feed efficiency and/or animal growth rate are significantly enhanced when the methods of the present invention are followed.

In one embodiment, the invention offers a method of improving or promoting the growth of an animal by administering to the animal a therapeutically effective amount of the single RR ractopamine isomer. More particularly, the ractopamine used in this form of the invention is the pure or substantially pure form of the RR-isomer of ractopamine. When pure or substantially pure RR-ractopamine is used as a growth promoter for livestock, it is possible to reduce the dose from the doses used for racemic ractopamine, thereby lowering costs handling and transports of the less bulky material. Lowering the dose will have the added advantage of lowering the tissue residues of the drug in the carcasses of the livestock animals. When using ractopamine in animals, the environmental impact will be reduced by using the pure or substantially pure RR-isomer rather than any of the enantiomeric pairs or any of the racemic mixtures of ractopamine, since neither of the RS—, SR— or SS-isomers or the metabolites thereof will pollute the environment.

It may be particularly beneficial to eliminate or reduce the administration of the distomeric RS—, SR— and SS-isomers of ractopamine to animals since the distomeric isomers may cause side-effects both in the animals and in humans eating such animals particularly since at least the SS-isomers is completely devoid of adrenergic beta-receptor stimulating activity and the RS— and SR-enantiomers have reduced beta-receptor activity when compared with RR-ractopamine as described in this document and in Shappell et al, 2000 (Shappell, N. W., Feil V. J., Smith D. J., Larsen G. L., McFarland D. C.: Response of C2C12 mouse and turkey skeletal muscle cells to the beta-adrenergic agonist ractopamine. J. Anim. Sci. 2000, 78: 699-708, which publication is hereby included in its entirety by reference.)

Furthermore, although there usually is some variability from one animal to another and from one species to another, by administering an effective amount of only the RR-isomer of ractopamine or at least substantially pure RR-isomer, it is possible to accomplish a more targeted treatment of the animals. In particular, this is important since it is not desirable to administer to animals, and particularly not to livestock animals, a compound with a multifaceted spectrum of pharmacological activities, pharmacological side effects and toxic effects. The term "a more targeted treatment" in this context means that by using the pure or substantially pure RR-isomer, the therapeutic activity of the RR-isomer can be taken advantage of without also having unwanted consequences of the RS—, SR— or SS-isomers.

In another embodiment, the present invention provides a method of improving the feed efficiency of an animal by administering to the animal a therapeutically effective amount of a pure or substantially pure RR-ractopamine preparation devoid or substantially devoid of the RS—, SR— and SS-isomers of ractopamine. More particularly, the ractopamine preparation used in this form of the invention is a pure or substantially pure form of the RR-isomer of ractopamine.

In still another embodiment, the invention provides a method of increasing the muscle to fat ratio in an animal by administering to the animal a therapeutically effective amount of a ractopamine preparation devoid or substantially devoid of at least the SS isomer of ractopamine. More particularly, the ractopamine preparation used in this form of the invention is a pure or substantially pure form of the RR-isomer of ractopamine, such forms being the free amine form or salt form or a solvate form of said RR-isomer.

In another embodiment, the present invention also provides a method to improve the financial returns for livestock producers, since low-fat carcasses can attract a premium price of more than 30 percent (International Egg and Poultry Revue, USDA, Aug. 2, 2005. www.ams.usda.gov/poultry/mncs/International PoutlryandEgg/2005Reports/x080205.pdf, which publication is hereby included in its entirety by reference.)

In a further embodiment, the present invention provides methods for prophylactic treatment of mammals with hereditary or environmental risks for the development of obesity with ractopamine. According to this embodiment, the present invention provides a method for reducing excessive fat in animals and humans in need thereof and in particular in obese companion animals and obese humans by administering to the subject in need thereof, an effective amount of a ractopamine preparation. More particularly, a ractopamine preparation used in this form of the invention may preferentially contain the pure or substantially pure RR-isomer of ractopamine. However racemic ractopamine will also cause weight loss in obese animals and will also have therapeutic value in the treatment of obesity in animals and in humans. The invention also relates to a method of treating obesity in animal, said method comprises administering an adrenergic beta-receptor agonist, such as ractopamine, in particular RR-ractopamine or the essentially pure RR-ractopamine combination with at least one additional compound of therapeutic value, in particular and anti-obesity drug, such as for example a cannabinoid-1 receptor antagonist, such as for example rimonabant, or a microsomal triglyceride transfer protein inhibitor, such as for example mitratapide or dirlotapide. Dirlotapide is presently marketed in the US as single-drug therapy for the treatment of obesity in companion animals under the name SLENTROL®, Pfizer. As an alternative to simultaneous co-administration of ractopamine+another active anti-obesity drug, the treatment of obese animals may alternate between therapeutically effective doses of for example ractopamine or an isomer thereof and dirlotapide, which will have the added advantage of improved therapy by avoiding or decreasing adrenergic receptor down-regulation. Obesity in companion animals is usually defined as such animals being 10% or more in overweight. The doses of the therapeutic compounds depend on the size and the species of the animals and the results sought and the efficacy of the compounds. Thus, oral doses of 0.1 to 100 mg of RR-ractopamine, one to four times daily may be an adequate dose-range for the treatment of most companion animals and oral doses of a cannabinoid-1 receptor antagonist may range from 1 mg to 100 mg, one to four times daily. The therapeutic dose of a cannabinoid-1 receptor antagonist, such as for example rimonabant, may range from 0.05 mg to 50 mg one to four times daily and the daily dose of a microsomal triglyceride transfer protein inhibitor, such as for example mitratapide may range from 0.05 mg to 50 mg. The recommended dose of the microsomal triglyceride transfer protein dirlotapide (Slentrol®, Pfizer) is up to 1 mg/kg body weight, twice daily and has to be adjusted after about 2 months when used as single-drug therapy in obese dogs (www.pfizerah.com/slentrol, which document is hereby incorporated in its entirety by reference). Reduction of obesity is known to improve health in all mammals and the therapy suggested here would be useful also in humans. The invention may also provide prophylactic treatment to mammals with hereditary or environmental risks for the development of obesity. Thus the present invention provides both symptomatic and prophylactic treatment for animals and humans suffering from obesity or at risk for developing obesity. Use of a single isomer of an adrenergic beta-receptor agonist, such as for example RR-ractopamine, has the added advantage over the corresponding racemate that drug residues and drug exposure is decreased, since obese mammals administered a pure and single eutomeric isomer are administered less drug than if they are given the corresponding racemic mixture. It should be kept in mind that distomeric isomers have pharmacological effects, pharmacological side effects and toxic effects, such as for example pro-inflammatory effects. There are also additional pharmacokinetic advantages by using the pure or substantially pure RR-isomer of ractopamine, relating to the activities at various adrenergic receptor sites, as well as sites for the intestinal absorption and the metabolism in the liver and elsewhere.

It is of particular importance to reduce or eliminate the use of the RS—, SR and SS-isomers of ractopamine since in the doses used in animals, these isomers are believed by the inventor not to carry any (SS and SR) or only limited (RS) growth promotant activity, but carry unwanted activities, such as for example risk for stress with concomitant decrease in meat quality and concomitant risk for lethality. There is a risk that pharmacological side effects and toxic effects of the RS—, SR— and SS— isomers of racemic ractopamine can be expressed in humans who have been eating meat from animals that have been administered racemic ractopamine, particularly if the racemic form of ractopamine is given in high doses to livestock animals. There may also be risks for unborn children and lactating infants when the mother eats meat treated with a mixture of ractopamine isomers, such risk being reduced or eliminated if the livestock animals are treated with the single RR-isomer of ractopamine rather than a racemic mixture of ractopamine or an enantiomeric pair of ractopamine. Thus, the present invention is reducing the risk for pharmacological side effects and toxic effects in humans, such side effects being hereinbefore described and originating from drug residues in animals, having been treated with a racemic mixture of ractopamine or an enantiomeric pair of ractopamine.

The use of the single RR-isomer of ractopamine or essentially pure RR-isomer in animal species, such as livestock species, and in humans, minimizes or eliminates any side effect that is the result of interaction by the SS—, RS— or SR-isomers of ractopamine with the efficacy, absorption, distribution, metabolism and excretion of RR-ractopamine.

Use of the methods of the present invention provides a means for improving the quality of meat from livestock animals by reducing stress and factors leading to stress, said stress being known to decrease the quality of meat (Sterle J.:

The Frequency of the Porcine Stress Gene in Texas Show Pigs. http://animalscience.tamu.edu.; Chatillon G. (1994): "Transport mortality has its origin in stress: how to get pigs to their destination in good condition. Porc. Magazine 265: 37-41; Warris P. D.; Brown S. N. and Adams S. J. M. 1994: "Relationship between subjective and objective assessment of stress a slaughter and meat quality in pigs. Meat Science 38: 329-340, which publications are hereby included in their entirety by reference).

Use of the methods of the present invention also provides a means of preventing or reducing morbidity, particularly attributable to stress, stress during transportation, aggressive interactions between animals and cardiovascular or respiratory events caused directly or indirectly as a consequence of the administration of the SS—, RS— or SR-isomers of ractopamine to the animals.

Use of the methods of the present invention also provides a means of preventing or reducing smooth muscle hyperactivity or hyperreactivity, as well as pro-inflammatory effects in mammals, caused directly or indirectly as a consequence of the administration of the SS—, RS— or SR-isomers of ractopamine to the mammal.

The environmental impact of dosing livestock animals with RR-ractopamine rather than racemic ractopamine will be significant since neither the RS—, SR and SS— isomers of ractopamine nor the metabolites thereof will pollute the environment. Additionally, a favourable environmental impact will come from the fact that the doses of RR-ractopamine by weight will usually be lower than the corresponding doses of racemic ractopamine.

The present invention also relates to food compositions including an admixture of food materials containing the pure or substantially RR-isomer of ractopamine. RR-ractopamine is preferentially administered to animals that are being given a diet, consisting of protein-containing food materials in order to build muscle mass in said animals. Accordingly, in another embodiment, the invention provides a protein-containing animal feed preparation, to which has been added pure or substantially pure RR-ractopamine. The amount of pure or substantially pure RR-ractopamine will be generally chosen to provide from about 1 to 500 ppm of the pure or substantially pure RR-isomer of ractopamine in said food material. The term "ppm" refers to "gram per ton" and 10 ppm equals 10 gram per metric ton.

The daily dose of RR-ractopamine to animals varies widely and depends on the animal species, the routes of administration and the effect sought. In general, the daily doses of RR-ractopamine to animals varies between 0.01 mg to 500 mg per day, of which the lowest doses are intended for small animals and the highest doses are intended for large mammals.

When the purpose is to supplement animal feed with a RR-ractopamine preparation (i.e. pure or substantially pure RR-ractopamine) as herein described, said animal feed supplement usually contains pure or substantially pure RR-ractopamine and a suitable carrier or diluent. Such feed can be prepared by initially admixing the ractopamine preparation with a suitable carrier or diluent. Carriers suitable for use to make up the feed supplement compositions may include the following: alfalfa meal, soybean meal, cottonseed oil meal, linseed oil meal, sodium chloride, cornmeal, cane molasses, urea, bone meal, corncob meal, rice kernel and the like. The carrier promotes a uniform distribution of the active ingredients in the finished feed into which the carrier is blended. It thus performs an important function by ensuring proper distribution of the active ingredient throughout the feed.

Of importance is that the feed to the animal contain proteins, the presence of which in feed is a well-known prerequisite for muscle growth in all species. The dietary protein requirements for various livestock species are well known for those skilled in the art. As an example, a maize-soybean meal diet, formulated to meet or exceed National Research Council (1990) recommendations for major nutrients can be used for broiler chicken, wherein the crude protein concentration should preferably not be less than 17 to 18 percent by weight of the feed.

If the supplement is used as a top dressing for feed, the carrier likewise helps to ensure uniformity of distribution of the active material across the top of the dressed feed.

If the intention is to supply animals with drinking water that is supplemented with a racemic or single-isomeric ractopamine preparation, a carrier can be prepared, containing a fixed concentration of ractopamine in a suitable volume of a fluid, such as water, which, in turn, can be added to the drinking water of the animals, by adding said carrier volume directly to the drinking water of the animal or by adding said carrier to an automatic drinking system for animals.

The preferred medicated swine feed generally contain from 1 to 200 grams of pure or substantially pure RR-ractopamine per metric ton of feed, the optimum amount for these animals usually being from 1 to 100 grams per ton of feed.

The preferred medicated drinking water for swine will generally contain from 1 to 100 ppm by weight of RR-ractopamine.

The preferred medicated feed for ruminants, such as for example cattle and sheep, generally contains from 5 to 500 grams of pure or substantially pure RR-ractopamine per ton of feed, the optimum amount for these animals usually being about 10 to 200 grams per ton of feed.

The preferred medicated drinking water for ruminants, such as for example cattle and sheep, generally contain 5 to 500 ppm by weight of RR-ractopamine.

The preferred medicated feed for birds, such as for example chicken and turkeys, generally contain from 1 to 100 grams of pure or substantially pure RR-ractopamine per ton of feed, the optimum amount for these animals usually being about 2 to 50 grams per ton of feed.

The preferred medicated drinking water for birds, such as for example chicken and turkeys, generally contain 1 to 50 ppm by weight of RR-ractopamine.

The magnitude of a therapeutic dose of RR-ractopamine to horses in the management of heaves will vary with the severity of the disease to be treated, and other conditions, such as for example the size of the animal. The dose of RR-ractopamine used to treat horses with heaves will offer an amount sufficient to alleviate bronchospasms but insufficient to cause adverse effects. The dose needed to obtain an optimal therapeutic effect will vary and will depend on the dose frequency and will also vary according to the age, body weight, and response of the individual horse. In general, the total daily dose ranges when administered by inhalation, for the conditions described herein, is from about 0.2 microgram to about 200 micrograms per kilogram bodyweight two or four times daily. Preferably, a daily oral dose range should be between about 0.2 milligrams to 200 milligrams, two to four times daily; all doses will have to be titrated according to the severity of the symptoms as well known by the caring veterinary staff. A controlled-release tablet may be more convenient than an instant-release tablet and may contain at least twice the amount of RR-ractopamine as an instant release tablet or for example between 4 and 400 mg RR-ractopamine. Part of the dose of RR-ractopamine in a controlled-release tablet may be contained in the coating of the tablet for immediate release and the remaining dose of RR-ractopamine may be contained in the core of the tablet for controlled release later. Controlled-release tablets may be given to the horse once or twice daily, while instant-release tablets may have to be given to the horse up to 4 times daily. In managing the horse suffering from heaves or from another bronchial ailment that includes bronchial smooth muscle constriction or hyperactivity, the therapy should be initiated at a lower dose, perhaps about twice daily dosing with 1 milligrams to about 12 milligrams and increased up to about twice daily dosage of 10 milligrams or higher depending on the horse's global response. It is further recommended that older horses and horses with impaired renal, or hepatic function, initially receive low doses, and that they be titrated based on individual response(s) and blood level(s). It may be necessary to use dosages outside these ranges as will be apparent to those skilled in the art. Further, it is noted that the treating veterinarian would know how and when to interrupt, adjust, or terminate therapy in conjunction with the individual horse's response. Analogous dosages and dosage forms apply to other animal species that may be administered RR-ractopamine to induce relief from bronchoconstriction.

In a particular embodiment of the methods of the invention, pure or essentially pure RR-ractopamine is administered in combination with at least one antibacterial agent. The term "antibacterial agent(s)" or "antibacterial compound(s)" or the like, as used herein, comprises various types of compounds and feed additives, such as compounds having bactericidal effects or bacteriostatic effects and compounds that in other ways protect from infections, such as for example immuno-stimulating compounds. Examples of immunostimulatory compounds are for example beta glucans or lipopolysaccharide-containing root extracts from the plant astragalus membranaceus. Other natural compounds, such as for example oil of oregan or carvacrol and medications, such as for example tilorone, which improve the immunological defence of the animals against infections by organisms such as for example virus, fungus, bacteria or parasites are also known and may be useful, particularly if used together. The doses of beta glucans vary among species and will also depend on the efficacy sought. The oral doses of beta glucans to swine and chicken are generally from 0.2 mg/kg bodyweight/day to 4 mg/kg bodyweight/day and are mixed into the feed of the animals, preferably 0.2 to 1.0 mg/kg bodyweight/day of beta glucans having a particle size of 1 micron or less. Antibacterial compounds, such as for example tylosin, bacitracin and lincomycin, can be used for the prevention of infections or for controlling or reducing infections and/or for promoting health or growth (growth promotion), and/or for decreasing mortality. As an example, tylosin may be administered for example to swine for control of proliferative enteropathies (ileitis) that is caused or associated with Lawsonia intercellularis, for improved feed efficiency and/or for improved lean/fat ratio (increased leanness.)

It has now been established that solutions containing water-soluble salt forms of racemic formulations of ractopamine in the drinking water are suitable for administration to animals, e.g. swine, cattle, sheep, horses, chicken, and turkeys. The concentrations of a water-soluble salt form of racemic ractopamine in the drinking water are within the limits stated above for medicated drinking water containing pure or essentially pure RR-ractopamine for swine, cattle, sheep, horses, chicken, and turkeys.

It has also been found that certain water-soluble but chirally stable salts of pure or essentially pure RR-ractopamine are well suited for administration in drinking water. The biologically active forms of ractopamine are also suitable for administration in implanted reservoirs, as for example reservoirs to be implanted into the rumen of cattle or sheep, as described in for example U.S. Pat. Nos. 6,855,334 and 6,974,587, which patents are hereby included in their entirety by reference.

Eutectic mixtures of the ractopamine isomers may have physicochemical and/or pharmacological and/or other advantages, such as for example manufacturing advantages or solubility advantages over racemic mixtures. Formulations containing biologically active eutectic mixtures of ractopamine isomers or enantiomeric pairs of ractopamine are included in the present invention.

It was surprisingly found that RR/SS ractopamine has advantages over a racemic mixture containing all four enantiomers. Thus, a racemic mixture of the RR— and SS-enantiomers, which contains approximately 50% of each of the enantiomers, is chemically and chirally stable and has metabolic and pharmacokinetic advantages, and the use of the RR/SS-ractopamine racemate is also reducing or eliminating side effects that are residing in the RS— and the SR-enantiomers. The enantiomeric pair RR/SS-ractopamine is more potent than a ractopamine racemate of all four isomers and the enantiomeric pair RR/SS-ractopamine may therefore be used in doses that are lower than a racemic mixture of all four isomers. The environmental impact of the RR/SS-ractopamine mixture is less than the impact of a racemate containing all four isomers. The concentrations of RR/SS-ractopamine in the feed of various animal species are within the frames for each species as stated above for RR-ractopamine. Water-soluble salt form of racemic RR/SS-ractopamine in the drinking water to livestock animals are within the limits for RR-ractopamine, as stated above for medicated drinking water for swine, cattle, sheep, horses, chicken, and turkeys. Thus, the RR/SS-ractopamine racemic mixture is useful as a growth promoter for livestock animals, for reducing fat deposits in animals and for improve the feed efficiency and thereby the economics of the animal livestock industry.

In another embodiment, the invention provides compositions and pharmaceutical formulations for the use of the RR/SS-ractopamine racemic mixture as a growth promoter for livestock, which includes a therapeutically effective amount of the pure or substantially pure racemic mixture RR/SS-ractopamine. The RR-enantiomer is expressing all or most of the growth-promoting activity of the enantiomeric pair RR/SS, while the presence of the SS-enantiomer will prevent racemization. Thus, in cases where there is risk for racemization of RR-ractopamine, RR/SS can be the preferred compound. The formulations to be used for the RR/SS racemic mixture are similar to the feed and drinking water formulations for RR-ractopamine, described herein, wherein RR/SS-ractopamine is used instead of RR-ractopamine. RR/SS-ractopamine can be co-administered with other compounds as described for RR-ractopamine above.

The terms "pure RR/SS-ractopamine", "pure RR/SS-racemate of ractopamine" and the like as used herein, indicate a enantiomeric purity of RR/SS-ractopamine that is 98%, or better, which means that pure RR/SS-ractopamine contains 98% by weight or more of RR/SS-ractopamine and 2% by weight or less of the sum of the RS— and SR-enantiomers.

The terms "substantially pure RR/SS-ractopamine", "substantially pure RR/SS-mixture of ractopamine" and the like as used herein, refer to enantiomeric purity that is 80% or better, which means that substantially pure RR/SS-ractopamine contains 80% by weight or more of RR/SS-ractopamine and 20% or less of the sum of the RS— and SR-enantiomers. In a more preferred embodiment the purity of substantially pure RR/SS-ractopamine is 90% by weight or better, which means 90% by weight or more of RR/SS-ractopamine and 10% by weight or less of the sum of the RS and SR enantiomers of ractopamine.

In still another embodiment the invention provides compositions and pharmaceutical preparations for use in above methods, which include a therapeutically effective amount of the pure or substantially pure racemate RR/SS ractopamine.

Eutectic mixtures of the RR and SS-enantiomers may have certain physicochemical, pharmacological and manufacturing advantages over racemic mixtures. Formulations containing eutectic mixtures of the RR— and SS-enantiomers are included in the present invention.

It was surprisingly found that mixtures of the two enantiomers RS-ractopamine and SR-ractopamine have advantages over a racemic mixture containing all four RR, RS, SR and SS isomers. Thus, an enantiomeric pair of the RS— and SR-enantiomers, which contains approximately 50% of each of the two enantiomers, has metabolic and pharmacokinetic advantages, and RS/SR-ractopamine is also completely devoid of any side effects that are exclusively residing in the RR— and the SS-isomers. It has been suggested that the SR-enantiomer contributes to the drug-induced increase more than the RS-enantiomer, despite the fact that RS-ractopamine has higher affinity for beta-receptors than the SR-enantiomer (Mills, Kissel et al., 2003). It has not been shown if this actually is the case in all species and in all types of tissues and the relative importance of RS and SR is therefore not known. However, one of the two enantiomers (RS or SR) is dominating (eutomeric) in various tissues or organs (or species) after administration of the enantiomeric pair RS/SR to animals and the main purpose for including both enantiomers is be sure that functional adrenergic beta-stimulation will occur and to prevent the racemization of the eutomer. The enantiomeric pair RS/SR-ractopamine is expressing stress in the animals to a lesser degree than the racemic mixture containing all four isomers. The environmental impact of RS/SR-ractopamine is significantly less than the impact of a racemate containing all four isomers. The concentrations of RS/SR-ractopamine in the feed of various animal species are within the frames for each species as stated above for RR-ractopamine. The concentration of a water-soluble salt form of RS/SR-ractopamine in the drinking water is within the limits stated above for RR-ractopamine in medicated drinking water for swine, cattle, sheep, horses, chicken and turkeys. In another embodiment, the invention provides compositions and pharmaceutical formulations for the use of the RS/SR-ractopamine racemic mixture as a growth promoter for livestock, which include a therapeutically effective amount of the pure or substantially pure enantiomeric pair RS/SR-ractopamine. The formulations to be used for RS/SR-ractopamine mixture is similar to formulations of RR-ractopamine in feed described herein, wherein RS/SR-ractopamine is used instead of RR-ractopamine. A eutectic mixture of the RS and SR-enantiomers has certain physicochemical, pharmacological and manufacturing advantages over racemic mixtures.

The terms "pure RS/SR-ractopamine", "pure RS/SR enantiomeric pair of ractopamine" and the like refer to an enantiomeric purity of RS/SR-ractopamine that is 98%, or better, which means that pure RS/SR-ractopamine contains 98% by weight or more of RS/SR-ractopamine and 2% by weight or less of the sum of the RR— and SS-enantiomers.

The terms "substantially pure RS/SR-ractopamine", "substantially pure RS/SR enantiomeric pair of ractopamine" and the like as used herein, refer to an optical purity of 80% or better, which means that substantially pure RS/SR-ractopamine contains 80% by weight or more of RS/SR-ractopamine and 20% by weight or less of the sum of the RR— and SS-isomers. In a more preferred embodiment the optical purity of substantially pure RS/SR-ractopamine is 90% by weight or better, which means 90% or more of RS/SR-ractopamine and 10% or less of the sum of the RR— and SS-isomers of ractopamine.

In still another embodiment, the invention provides compositions and pharmaceutical preparations for use in above methods, which include a therapeutically effective amount of pure or substantially pure RS/SR ractopamine as shown above for RR-ractopamine.

A eutectic mixture of the RS and SR-enantiomers has certain physicochemical, pharmacological and manufacturing advantages over racemic mixtures. Formulations containing eutectic mixtures of the RS— and SR-enantiomers are included in the present invention.

In the present method, the various forms of ractopamine—including RR-ractopamine and the enantiomeric pairs described above—can be administered by any suitable means, including parenterally, transdermally, subcutaneously, intravenously, intramuscularly or orally, topically, nasally, rectally, by inhalation or via implanted reservoirs or pellets containing the drug. The preferred route of administration is the oral route, with the drug mixed into the feed or the drinking water of animals.

When administered in the feed or in the drinking water, the active ingredient (for example RR-ractopamine) is prepared as a powder or as a granulate, by methods known to those skilled in the art. Powders may be sifted and/or milled as is also known to those skilled in the art. The powder/granulate is mixed into a carrier as previously described. The carrier or a carrier/feed mixture material may be sold commercially for final mixing into the animal feed by the end-user. Since RR-ractopamine has a short biological half-life, no withdrawal period is needed and RR-ractopamine can be fed to the livestock animals until the day of slaughter.

The form in which the drug will be administered (e.g. injectables, inhalants, powders, granulates, tablets, capsules, solutions, emulsions, subcutaneous pellets, transdermal patches, suppositories, sprays, aerosols or reservoirs to be implanted into the rumen of cattle or sheep, etc.) will depend on the route by which it is administered. The drug, as for example RR-ractopamine, may be administered orally in tablets, granulae, powder, capsules, caplets, solutions, suspensions or similar forms. Formulations for oral use may contain the active ingredient(s) in admixture with non-toxic pharmaceutically acceptable excipients. These excipients may be, for example, inert diluents, such as calcium carbonate, sodium chloride, lactose, calcium phosphate or sodium phosphate; granulating and disintegrating agents, for example, potato starch or alginic acid; binding agents, for example, starch, gelatine or acacia; and lubricating agents, for example, magnesium stearate, stearic acid or talc. Other pharmaceutically acceptable excipients can be colorants, flavouring agents, plasticizers, humectants etc. Tablets may be uncoated or they may be coated by known techniques, optionally to mask taste, delay disintegration and absorption in the gastrointestinal tract and thereby provide a sustained action over a longer period (i.e. controlled release). For example, a time delay material such as glyceryl monostearate or glyceryl distearate may be employed.

Formulations for oral use of RR-ractopamine or any of the racemates described herein may also be presented as chewing tablets, or as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

Powders, dispersible powders or granules suitable for preparation of an aqueous suspension by addition of water are also convenient dosage forms of the present invention. Formulation as a suspension provides the active ingredient in admixture with a dispersing or wetting agent, suspending agent and one or more preservatives. Suitable dispersing or wetting agents are, for example, naturally-occurring phosphatides, as e.g. lecithin, or condensation products of ethylene oxide with e.g. a fatty acid, a long chain aliphatic alcohol or a partial ester derived from fatty acids and a hexitol or a hexitol anhydrides, for example, polyoxyethylene stearate, polyoxyethylene sorbitol monooleate, polyoxyethylene sorbitan monooleate etc. Suitable suspending agents are, for example, sodium carboxymethylcellulose, methylcellulose, sodium alginate etc.

Additionally, other preferred forms of administration are by inhalation or by transdermal delivery systems or subcutaneous delivery systems, which will reduce or avoid gastrointestinal metabolism and hepatic first-pass metabolism by metabolizing enzymes; such delivery systems may be designed to prolong the absorption or decrease the peak plasma drug concentration or to increase the exposure of the animal to the drug (increased AUC, meaning Area Under a Curve where plasma drug concentration has been plotted over time).

Preparations of RR-ractopamine or any of the enantiomeric pairs described herein may also be administered parenterally (intravenous, intramuscular, subcutaneous or the like) in dosage forms or formulations containing conventional, non-toxic pharmaceutically acceptable carriers and adjuvants. The formulation and preparation of such compositions is well known to those skilled in the art of pharmaceutical formulations. Additional information can be obtained in medical and pharmaceutical textbooks, such as for example Goodman & Gilman: The Pharmacological Basis of Therapeutics. Section 1. McGraw-Hill, Ed 9, ISBN 0-07-026266-7. For parenteral use, the pharmaceutical compositions according to the invention may comprise the preparation in the form of a sterile injection. To prepare such a composition, the preparation is dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl or n-propyl p-hydroxybenzoate.

For parenteral administration ractopamine preparations may be prepared in the form of a paste or pellet and administered as an implant, usually under the skin of the head or ear of the animal in which increase in lean meat deposition and improvement in lean meat to fat ratio is sought.

As an alternative to a paste, pellet or subcutaneous implant, parenteral administration may involve injection of a solution, containing sufficient amount of the pure or substantially pure RR-ractopamine to provide the animal with 0.1 to 100 mg/day of the active ingredient. Preferred parenteral dosages for swine, cattle, and sheep are in the range of from 0.5 to 100 mg/day of pure or substantially pure RR-ractopamine; whereas, the preferred dose level of said parenteral ractopamine preparation for chicken and turkeys are in the range of from 0.05 to 20 mg/day.

For the rectal application, suitable dosage forms for a composition according to the present invention include suppositories (emulsion or suspension type), and rectal gelatin capsules (solutions or suspensions). In a typical suppository formulation, the ractopamine preparation is combined with an appropriate pharmaceutically acceptable suppository base such as cocoa butter, esterified fatty acids, glycerinated gelatin, and various water-soluble or dispersible bases like polyethylene glycols and polyoxyethylene sorbitan fatty acid esters. Various additives like e.g. enhancers or surfactants may be incorporated.

For the nasal application, typical dosage forms for a composition according to the present invention include nasal sprays and aerosols. In a typical nasal formulation, the active ingredients are dissolved or dispersed in a suitable vehicle. The pharmaceutically acceptable vehicles and excipients and optionally other pharmaceutically acceptable materials present in the composition such as diluents, enhances, flavouring agents, preservatives etc. are all selected in accordance with conventional pharmaceutical practice in a manner understood by the persons skilled in the art of formulating pharmaceuticals.

The ractopamine preparations according to the invention may also be administered topically on the skin for percutaneous absorption in dosage forms or formulations containing conventionally non-toxic pharmaceutically acceptable carriers and excipients that may include microspheres and liposomes. The ractopamine preparations include creams, ointments, lotions, liniments, gels, hydrogels, solutions, suspensions, pastes, plasters and other kinds of transdermal drug delivery systems. The ractopamine preparations may include emulsifying agents, antioxidants, buffering agents, preservatives, humectants, penetration enhancers, chelating agents, gel forming agents, ointment bases, perfumes and skin protective agents.

The quantity of the drug to be administered to an animal will have to be titrated for each species. In general, the doses of the RR-ractopamine preparation to be used in swine may—as an example—be about 2 to 10 ppm, e.g. about 5 ppm of RR-ractopamine included in the feed for swine. With a total treatment period of 28 days and 20 to 100 mg/head/day, e.g. about 50 mg/head/day, this corresponds to a total consumption of 0.56 to 2.8 grams, e.g. about 1.4 grams of RR-ractopamine for each swine. It is usually calculated that finishing swine have a feed consumption of 3 kg/day. The doses of the RR-ractopamine preparation to be used in cattle may—as an example—be about 20 ppm of RR-ractopamine in feed for cattle and a treatment period of 28 days and 200 mg/head/day, this corresponds to a total consumption of 5.6 grams of RR-ractopamine for each cow. It is usually calculated that finishing cattle have a feed consumption of 10 kg/day. The total consumption of RR-ractopamine will be decreased or increased with changes in the feed inclusion of RR-ractopamine and with changes in the duration of the treatment period. The daily dose of RR-ractopamine to cattle may be as high as 500 mg/head/day. It is common and it may be found advantageous to change the feed inclusion of RR-ractopamine during the treatment period and all changes in the doses administered to the animals will of course influence the total consumption per animal of active ingredient.

Since RR-ractopamine has a short biological half-life, no withdrawal period is needed and RR-ractopamine can be fed to the animals until the day of slaughter.

It may be advantageous to administer RR-ractopamine as an implantable subcutaneous controlled-release pellet, designed to deliver from 1 mg/day to 300 mg/day for the entire treatment period, which may last up to six or eight weeks, whereupon the animal may be slaughtered without any withholding period (drug-free days before slaughter) or with a short withholding period of one to three days. For all livestock species, the doses of RR-ractopamine have to be carefully titrated and will depend on the pharmacological efficacy of the drug in the selected species or sub-species, the metabolic fate and rate of excretion of the drug in various species, the route of administration, the size of the animal and the results sought. In general, quantities of growth promotant sufficient to decrease body fat, increase muscle mass, and improve feed efficiency will be administered. The actual dosage (quantity administered at a time) and the number of administrations per day will depend on the pharmacokinetic property of the drug and the metabolism of the drug in the body of the specific animal species. For example about 10 to 3000 micrograms of the pure RR-isomer of ractopamine may be given by various forms of inhalation devices, such as metered dose inhalers and nebulizers, 0.01 to 500 milligrams may be given by the oral route (for example as powders, granulates, tablets or liquids) one to four times per day (or as ad lib daily doses to animals) and may be an adequate dose in most livestock animals to produce the desired effect. Suitable oral doses in humans include doses in the range of 0.05 mg to 5 mg once daily or said doses given repeatedly up to six times during the day. The actual and finally titrated drug doses may be higher or lower and administration may take place more or less frequently than indicated above, as determined by clinical studies or by the caring individual, physician or veterinarian.

Sterile solutions for use in nebulizers are supplied in unitedose, low-density polyethylene (LDPE) vials as a clear, colourless, sterile, preservative-free, aqueous solution containing different doses of RR-ractopamine (0.63 mg, 1.25 mg, 5 mg, etc.). The concentrations shown here are examples only. Other concentrations may be manufactured for use by the caring veterinary staff. Metered dose dispensers may contain the API (RR-ractopamine) as a solution or as a micronized suspension.

| Formula | Quantity Contained in Each Metered Dose Dispenser 7.5 ml (10.5 g) Canister |
|---|---|
| RR-ractopamine (free amine) | 1.8 mg |
| Trichloromonofluoromethane | 5.16 g |
| Dichlorodifluoromethane | 5.16 g |
| Sorbitan trioleate | 0.105 g |

Each actuation delivers 90 mcg of RR-ractopamine. Multiple actuations will be given to the horse for acute treatment of airway obstruction. Alternatively, devices that deliver larger volumes of RR-ractopamine can be used. Metered dose dispensers may also dispense the API as a dry powder, as is well known to those skilled in the art.

It is recognized that more than one pellet, tablet or dose may be administered to an animal to achieve the desired dose level which will provide the increase in lean meat production and improvement in lean meat to fat ratio desired. Moreover, it has been found that implants may also be made periodically during the animal treatment period in order to maintain the proper drug level in the animal's body.

The pharmacological side effects of RR-ractopamine in high dose include tremor and tachycardia. These and other side effects may be of short duration and may be associated with peak plasma concentrations of the drug in connection with a drug overdose. These side effects can be reduced or completely avoided by admixture of the RR-ractopamine formulation into the feed or the drinking water of livestock animals or by using drug delivery systems that slowly release the drug of the present invention into the systemic circulation. Such slow-release or controlled-release delivery systems include granulae, tablets, capsules, subcutaneous pellets or forms of reservoir depots with slow-release or controlled-release properties that are designed to release the active ingredient slowly or in a controlled manner.

In the method of the present invention, the RR-isomer of ractopamine or either of the RR/SS or the RS/SR enantiomeric pairs of ractopamine can be administered together with one or more other active compound(s). Compounds that improve or prolong the therapeutic effect of beta-agonists, e.g. compounds that delay or inhibit the absorption or the metabolic degradation of the compound, may also be co-administered with the adrenergic beta-receptor agonist to further improve the therapeutic activity. Other drugs such as for example other growth promoting agents and antibacterial compounds may be combined with the selected drug of the present invention to obtain improved health of the animal or improved growth-promotant activity of the formulation.

Antibacterial agents may be used together with compounds of the present invention in order to prevent or control infections by bacteria, virus, fungus and/or parasites or to improve on possible antibacterial effects of the compounds of the present invention. Antibacterial compounds also have growth promoter activity by unknown mechanisms of action. Thus antibacterial agents may increase or promote or potentiate the effects of the compounds of the present invention on fat reduction, muscle growth and/or feed efficiency.

Eutectic mixtures containing RR-ractopamine and another active component or other active components may be used and may have certain biological advantages, such as for example leanliness (muscle/fat), pharmacokinetic or metabolic advantages or may have improved side effects or improved receptor activity as realized by those skilled in the art of chiral drug pharmacology. Eutectic mixtures of RR-ractopamine+SS-ractopamine or of RS-ractopamine+SR-ractopamine can also be expected to have certain advantages, such as for example improved receptor activation, improved water solubility, improved chiral stability and/or facilitated manufacturing.

RR-ractopamine can be used for weight loss therapy and will cause loss of fat tissue in obese animals and humans. When used for weight-loss purposes, the administration of RR-ractopamine should preferably be combined with appropriate life-style modifications, such as for example modified eating habits and increased exercise. RR-ractopamine can also be combined with other anti-obesity drugs having the same mechanisms of action as RR-ractopamine, or different mechanisms of action.

Chemistry

Racemic ractopamine can be made by methods that are obvious to those skilled in the art of chemistry. A synthetic method was described by van Dijk J. and Moed H. D. in Recueil des Travaux Chimiques, 1973, Vol. 92: 1281-1297 and is hereby included in its entirety by reference. A synthetic method for ractopamine was also described by Anderson D. B. et al. (Eli Lilly): Growth Promotion. U.S. Pat. No. 4,992, 473, which is hereby included in its entirety by reference.

Racemic ractopamine can also be isolated and purified from conveniently available commercial sources. One kilogram of commercially available Paylean® (Elanco) was stirred overnight with 15 L of water. The mass was filtrated, and the filtrate (11.5 L) was evaporated under reduced pressure to a small volume (ca. 1-2 L). Aqueous potassium carbonate was added to raise pH to ca. 10, and the solution was extracted twice with equal volumes of ethyl acetate. The ethyl acetate extracts were combined, evaporated under reduced pressure to ca. 0.5 L, and an equal volume of hexanes added. After standing overnight, crystals of ractopamine free base (6.83 g) were filtrated. This material was crystallized again from ethyl acetate/hexanes to give pure ractopamine free base (6.01 g). HPLC showed 98.5% purity. A sample of ractopamine free base (120 mg) was stirred with 10 ml of deionized water cooled in an ice-water bath, and 2 M aqueous hydrochloric acid (2 ml) was added slowly. After stirring to dissolve the material, the solution was filtered and lyophilised to give ractopamine hydrochloride (125 mg). The mp was 128-135° C., lit (Merck Index) mp 124-129° C. $^1$H NMR was consistent. HPLC showed 98.0% chemical purity.

The RR-isomer of ractopamine can also be obtained by stereoselective synthesis, using optically active starting material(s) as know to those skilled in the art of synthetic chemistry and as described by Van Dijk et al. (Van Dijk J. and Moed H. D. in Recueil des Traveaux Chimiques, 1973, 92: 1281-1297), which publication is hereby incorporated in its entirety by reference.

The ractopamine isomers can be synthesized according to the methodology of Ricke et al., 1999, which is hereby included by reference in its entirety (Ricke E A, Smith D J, Feil V J, Larsen G L, Caton J S: Effects of ractopamine HCl stereoisomers on growth, nitrogen retention and carcass composition in rats. J. Anim, Sci.1999. 77:701-707, which publication is hereby included in its entirety by reference)

The stereoisomeric compound to be used may be separated from the other stereoisomers by means of techniques known per se, for example, selective crystallization of an addition salt with a stereoisomer of an acid with a chiral center. However, stereoselective synthesis, using a stereochemically pure starting material or a stereochemically pure intermediate product can also be used.

Methods for the preparation of RR-ractopamine have been described by Mills J. et al. in Eur. Pat Appln 7,205 and by Anderson D. B. et al. in U.S. Pat. No. 4,690,951, both of which are hereby incorporated in their entirety by reference. Additional information is available in chemical literature, such as for example: Stereochemistry of Carbon Compounds, E. L. Eliel, McGraw Hill 1962; "Tables of Resolving Agents," S. A. Wilen and Lochmuller, L. H. et al., 1975, J. Chromatogr. 113(3): 283-302, which publication is hereby included in its entirety by reference. Additionally, a method for the preparation of RR-enantiomeric phenethanolamines was described by Anderson D. B. et al. in Growth Promotion, U.S. Pat. No. 5,643,967, which patent is hereby included by reference in its entirety.

Biological Effects

Background

The growth promotant activity of the adrenergic beta-receptor agonist ractopamine has been demonstrated in various livestock species. See for example: Watkins L. E.; Joens D. H.; Mowrey D. H.; Anderson D. B. and Veenhuizen L. 1990: "The effect of various levels of ractopamine hydrochloride on the performance and carcass characteristics of finishing swine." J. Anim. Sci. 68: 3588-3595; Williams N. H.; Cline T. R.; Schinkel A. P. and Jones D. J. 1994: "The impact of ractopamine, energy intake and dietary fat on finisher pig growth performance and carcass merit." J. Anim. Sci. 72: 3152-3162; Mills S. E.: 2001: "Biological Basis of Ractopamine Response." J. Anim. Sci. 79 (Suppl. 1): E28-32; Marchant-Forde J. N., Lay D. C., Pajor E. A., Richert B. T., Schinckel A. P.: The effects of ractopamine on the behavior and physiology of finishing pigs. J Anim Sci. 2003, 81: 416-422 which publications are all hereby included in their entirety by reference.

To those skilled in the art of pharmacology, it is known that synthetic adrenergic beta-receptor agonists have numerous effects, that may have similarities to endogenous adrenergic beta-receptor agonists, of which adrenaline and noradrenaline are the most well known.

Three types of adrenergic beta-receptors have been described: Stimulation of beta-1 receptors leads—for example—to increased heart rate, increased cardiac contractility and increased blood pressure. Stimulation of adrenergic beta-2 receptors leads—for example—to relaxation of various types of smooth muscles, such as bronchial smooth muscle. Adrenergic beta-3-adrenergic receptors are—for example—involved in the regulation of lipolysis and thermogenesis. The binding of an agonist to a receptor does not always induce a signalling event and it is possible that an isomer may have affinity for a receptor-type without causing an increase in cyclic AMP in some organ, which may be caused by various factors, as known to those skilled in the art of pharmacology.

Adipose tissue has adrenergic beta-1, beta-2 and beta-3 receptors and stimulation of these receptors usually leads to lipolysis, which means that fat molecules are broken down. Stimulation of beta-receptors has also been shown to inhibit lipogenesis, which means that stimulation of these receptors can inhibit the formation of fat. Adrenergic beta-receptor stimulation is also known to increase muscle mass by a mechanism that is believed to involve inhibition of protein breakdown in the continuously ongoing process of formation and degradation of muscle proteins (Bardsley R G, Allcock S M J, Dawson J M, Dumelow N R, Higgins J A, Lasslett Y V, Lockley A K, Buttery P J Effect of β-agonists on expression of calpain and calpastatin activity in skeletal muscle. Biochimie, 1992, 74:267-273, which publication is hereby included in its entirety by reference.) Other mechanisms for the increase in muscle mass have been suggested and involve an induction of increased synthesis of proteins by adrenergic beta-receptor agonists. Thus, stimulation of adrenergic beta-receptors at various locations in the body will lead to decreased fat deposits and increased muscle mass.

Racemic ractopamine stimulates adrenergic beta-1 and beta-2 receptors, but neither racemic ractopamine nor any of the ractopamine isomers had affinity for adrenergic beta-3 receptors in the present studies.

In receptor binding studies, it has now been found that RR-ractopamine has the highest affinity for adrenergic beta-receptors among the four ractopamine isomers. RR-ractopamine is also having higher affinity for adrenergic beta-1 and beta-2 receptors than found for the racemic mixture of all four isomers. Also, the effects of the enantiomeric pairs RR/SS and RS/SR were less than that of RR-ractopamine. Interesting and important advantages of receptor selectivity by RR-ractopamine were found.

Those skilled in the art of pharmacology avoid linking of in vivo activity of adrenergic beta-agonists directly to receptor affinity of drugs, since the ultimate effects in vivo depend not only on receptor affinity, but also on the availability and composition of the available receptor population in various organs. The complicated situation in various organs can be exemplified with the availability of β-1 and β-2 receptors in the human heart, where, under normal circumstances, the distribution of adrenergic beta-receptors are approximately 77% β-1 receptors+23% β-2 receptors. Adrenergic receptor populations can change under various circumstances and during heart failure the human heart has less β-1 receptors than normal, and as a result the beta-receptor population in the failing heart consists of about 60% β-1 receptors + about 40% β-2 receptors (Bristow M R, Ginsburg R, Umans V, Fowler M, Minobe W, Rasmussen R, Zera P, Menlove R, Shah P, Jamieson S, Stinson E. β-1 and β-2 adrenergic receptor subpopulations in nonfailing and failing human ventricular myocardium. Circ Res 1986, 59: 297-309, which publication is hereby included in its entirety by reference.) Thus a combined beta-1/beta-2 receptor agonists may have advantages over a selective beta-1 or a selective beta-2 agonist. Adrenergic beta-receptors may also be down-regulated in selected organs upon repeated stimulation with an adrenergic agonist. The term "down-regulated" refers to the fact that individual receptors seem to disappear from the cell membrane, probably by internalisation into the cell. A decreased beta-receptor density by beta-adrenergic stimulation was described by Spurlock et al., who found that the concentration of adrenergic beta-receptors in adipose tissue could be reduced by 50% by exposing animals to racemic ractopamine. (Spurlock M E, Cusumano J C, Ji Q, Anderson D B, Smith-II C K, Hancock D L, Mills S E. The effect of ractopamine on β-adrenoceptor density and affinity in porcine adipose and skeletal muscle tissue. J. Anim, Sci. 1994, 72:75-80, which publication is hereby included in its entirety by reference.)

The following studies have been initiated by us and are performed in laboratory animals under our close supervision:

Example 1

Neuropharmacological profile studies are performed in laboratory animals (Irwin test) being repeatedly administered the test articles orally. Racemic ractopamine produced increased stress in the animals, thereby supporting the findings of Marchant-Forde et al. (Marchant-Forde J. N., et. al. 2003: "The effects of ractopamine on the behaviour and physiology of finishing pigs" J Anim Sci., 81: 416-422 and hereby included in its entirety by reference). Surprisingly the pure RR-isomer of ractopamine did not cause stress in this study. In the present Irwin tests, there was no stress by a reference compound (R-salbutamol; Cipla Batch #HX0247; gift from Dr. Y. Hamied) that is known not to cause stress in livestock animals (London et al., 2005), thereby validating the test methodology.

Example 2

Results from ongoing stress testing of RR-ractopamine, racemic ractopamine and R-salbutamol in mice using the methodology described by Aberg (U.S. Pat. No. 6,372,799) demonstrate CNS-mediated stress in animals treated with racemic ractopamine, while surprisingly, RR-ractopamine is not causing stress. Other isomers and enantiomeric pairs of ractopamine are studied using this methodology.

Example 3

Spontaneous motor activity studies in mice being administered test articles orally, were part of the Irwin tests (Example 1, above). As known by those skilled in the art, increased stress will produce increased spontaneous motor activity in mice. There were no statistically significant effects of RR-ractopamine on spontaneous motor activity in these studies.

Example 4

Airway smooth muscle tissues were contracted by carbachol. The inhibitory effects of isomers, enantiomeric pairs and a racemic mixture of ractopamine are being investigated. Conclusions (from ongoing studies): RR-ractopamine, but not SS-ractopamine demonstrates potent airway smooth muscle relaxing activity. The very weak activity of SS-ractopamine in this study is probably due to optical impurities of (a) more potent isomer(s) and/or to a weak intrinsic activity of SS-ractopamine. Racemates of ractopamine are significantly less active than RR-ractopamine. Test results from these functional studies verify and support the results from the receptor binding studies.

Example 5

Metabolic studies are being performed using hepatocytes and liver microsomes. Preliminary results indicate that the RR-isomer is metabolised at a higher rate than the SS-isomer. The metabolic rate of all single isomers, the two enantiomeric pairs and the racemic mixture of all isomers are being studied. Conclusions from current biological tests: Racemic ractopamine is causing symptoms that are indicative of CNS-mediated stress, while it has surprisingly been found the pure RR-isomer of ractopamine does not cause CNS-mediated stress in animals at dose-levels that are equivalent to therapeutic dose levels in vivo in livestock animals.

It is concluded from tests on bronchial smooth muscle—an in vitro model of bronchoconstriction in horses, suffering from heaves—that RR-ractopamine is a potent bronchodilator, useful in horses suffering from heaves.

Although the present invention has been described with reference to certain preferred embodiments, it will be appreciated that many variations and modifications may be made within the scope of the broad principles of the invention. Hence, it is intended that the preferred embodiments and all of such variations and modifications be included within the scope and spirit of the invention, as defined by the claims.

REFERENCES

The following publications and patents are hereby included in their entirety by reference.

Anderson D. B. and Veenhuizen L: The effect of various levels of ractopamine hydrochloride on the performance and carcass characteristics of finishing swine. J. Anim. Sci. 1990, 68: 3588-3595.

Bardsley R G, Alcock S M J, Dawson J M, Dumelow N R, Higgins J A, Lasslett Y V, Lockley A K, Buttery P J: Effect of β-agonists on expression of calpain and calpastatin activity in skeletal muscle. Biochimie, 1992, 74:267-273.

Boissy, A, Bouissou, M-F: Assessment of individual differences in behavioural reactions to heifers exposed to various fear-eliciting situations. Applied Animal Behaviour Science 1995, 46:17-31.

Bristow M R, Ginsburg R, Umans V, Fowler M, Minobe W, Rasmussen R, Zera P, Menlove R, Shah P, Jamieson S, Stinson E: β-1 and β-2 adrenergic receptor subpopulations in nonfailing and failing human ventricular myocardium. Circ Res 1986, 59: 297-309.

Eliel et al.: Stereochemistry of Carbon Compounds, Mc Graw Hill, 1962.

Chatillon G: Transport mortality has its origin in stress: how to get pigs to their destination in good condition. Porc. Magazine 1994, 265: 37-41.

Colbert W E, Williams P D, Williams G D: Beta-adrenoceptor profile of ractopamine HCl in isolated smooth muscle and cardiac muscle tissues of rat and guinea pig, J Pharm Pharmacol 1991, 43: 844-847.

Goodman-Gilman, The Pharmacological Basis of Therapeutics. 9th Ed., McGraw-Hill 1996. ISBN 0-07-026266-7.

Grandin, T (1993), Behavioural agitation during handling of cattle is persistent over time. Applied Animal Behaviour Science 1993, 36:1-9.

International Egg and Poultry Revue, USDA, Aug. 2, 2005. www.ams.usda.gov/poultry/mncs/InternationalPoutlryandEgg/2005Reports/x080205.pdf London C J, Aberg G., Sadler M., Marchant-Forde J N: Effects of a New Growth Promoter (R-albuterol) for Commercial Swine Production. Abstr. Bio2005, Philadelphia, US. June 2005.

Marchant-Forde J. N., Lay D. C., Pajor E. A., Richert B. T., Schinckel A. P.: The effects of ractopamine on the behavior and physiology of finishing pigs. J Anim Sci. 2003, 81: 416-422.

Merck Index, 1996, 12: Ractopamine; pages 1392-1393.

Mills S E: Biological Basis of Ractopamine Response. J. Anim. Sci. 2001, 79 (suppl1): E28 32.

Mills S E, Kissel J, Bidwell C A, Smith D J: Stereoselectivity of porcine β-adrenergic receptors for ractopamine stereoisomers. J. Anim. Sci. 2003, 81: 122-129.

Mills S E, Spurlock M E, Smith D J: Beta-adrenergic receptor subtypes that mediate ractopamine stimulation of lipolysis. J. Anim. Sci. 2003, 81: 662-668.

National Research Council. 1990. Metabolic modifiers—Effects on the nutrient requirements of food-producing animals. National Academy of Sciences, Washington D.C., USA.

Odeh F M, Cadd G G, Satterlee D G: Genetic characterization of stress responsiveness in Japanese quail. Poult Sci. 2003, 82: 31-35.

Post J, Rebel J M J, ter Huurne A A: Physiological Effects of Elevated Plasma Corticosterone Concentrations in Broiler Chicken. An Alternate Means by which to Assess the Physiological Stress. Poultry Science, 2003, 82:1313-1318.

Ricke E A, Smith D J, Feil V J, Larsen G L, Caton J S Effects of ractopamine HCl stereoisomers on growth, nitrogen retention and carcass composition in rats. J. Anim, Sci.1999. 77: 701-707.

Shappell, N. W., Feil V. J., Smith D. J., Larsen G. L., McFarland D.C.: Response of C2C12 mouse and turkey skeletal muscle cells to the beta-adrenergic agonist ractopamine. J. Anim. Sci. 2000, 78: 699-708.

Spurlock M E, Cusumano J C, Ji Q, Anderson D B, Smith-II C K, Hancock D L, Mills S E. The effect of ractopamine on β-adrenoceptor density and affinity in porcine adipose and skeletal muscle tissue. J. Anim, Sci. 1994, 72: 75-80.

Stadler K,: Porcine Stress Syndrome and Its Effects on Maternal, Feedlot and Carcass Quantitative and Qualitative Traits. The University of Tennessee, Agricultural Extension Service, PB 1606.

Thompson, M J; Huss, P; Unverferth, M D; Fasola A; Leier, C V: Hemodynamic effects of intravenous butopamine in congestive heart failure. Clin Pharmacol Ther, 1980, 28: 324-334.

Sterle J.: The Frequency of The Porcine Stress Gene in Texas Show Pigs. http://animalscience.tamu.edu.

Van Dijk J. and Moed H. D. in Recueil des Traveaux Chimiques, 1973, 92: 1281-1297.

Warris P D, Brown S N, Adams S J M. Relationship between subjective and objective assessment of stress a slaughter and meat quality in pigs. Meat Science 1994, 38:329-340.

Watkins L E, Jones D H, Mowrey D H, Anderson D B, Veenhuizen L. The effect of various levels of ractopamine hydrochloride on the performance and carcass characteristics of finishing swine. J. Anim. Sci. 1990. 68: 3588-3595.

Wilen, S A, Lochmuller, L H et al., 1975, J. Chromatogr. 113(3): 283-302.

Williams N H, Cline T R, Schinkel A P, Hones D L: The impact of ractopamine, energy intake and dietary fat on finisher pig growth performance and carcass merit. J. Anim. Sci. 1994, 72: 3152-3162.

EP 7,205
U.S. Pat. No. 4,690,951
U.S. Pat. No. 5,057,427
U.S. Pat. No. 5,077,217
U.S. Pat. No. 5,643,967
U.S. Pat. No. 6,372,799
U.S. Pat. No. 6,855,334
U.S. Pat. No. 6,974,587
WO 2006/064283 A1

The invention claimed is:

1. A method of minimizing the amount of tissue residue of total ractopamine in a ractopamine-treated animal, which comprises administering to the animal an effective amount of a pure or substantially pure RR-enantiomer of ractopamine or a pharmaceutically acceptable salt, solvate or polymorph thereof.

2. The method of claim 1, wherein the administration of the effective amount of the pure or substantially pure RR-enantiomer of ractopamine or a pharmaceutically acceptable salt, solvate or polymorph thereof, reduces the risk for pharmacological side effects and toxic effects in the animal.

3. The method of claim 1, wherein the administration of the effective amount of the pure or substantially pure RR-enantiomer of ractopamine or a pharmaceutically acceptable salt, solvate or polymorph thereof to the animal, reduces the risk for pharmacological side effects and toxic effects in a human that consumes meat from the animal.

4. The method of claim 1, wherein the administration of the effective amount of the pure or substantially pure RR-enantiomer of ractopamine or a pharmaceutically acceptable salt, solvate or polymorph thereof, reduces the environmental impact of the ractopamine treatment.

5. The method of claim 1, wherein the effective amount of the pure or substantially pure RR-enantiomer of ractopamine or a pharmaceutically acceptable salt, solvate or polymorph thereof is administered in combination with an effective amount of at least one antibacterial compound.

6. The method of claim 5, wherein the antibacterial compound is tylosin.

7. The method of claim 1, wherein the animal is an animal that is bred for human food.

8. The method of claim 1, wherein the animal is a ruminant.

9. The method of claim 1, wherein the animal is a livestock animal, bird or fish.

10. The method of claim 9, wherein the animal is a livestock animal.

11. The method of claim 9, wherein the animal is a swine.

12. The method of claim 9, wherein the animal is a cattle animal.

13. The method of claim 1, wherein the animal is a cattle animal, sheep, horse, swine, deer, bird, farmed fish or farmed crustacean.

14. The method of claim 1, wherein the animal is a chicken, turkey, duck, quail or goose.

15. A feedstuff composition formulated for administration to an animal, comprising an admixture of protein-containing feed material, an effective amount of a pure or substantially pure RR-enantiomer of ractopamine or a pharmaceutically acceptable salt, solvate or polymorph thereof, and an effective amount of the antibacterial compound tylosin.

16. The feedstuff composition of claim 15 that is formulated for administration to swine, cattle or turkeys.

17. The feedstuff composition of claim 16 that is formulated for administration to swine.

18. The feedstuff composition of claim 16 that is formulated for administration to cattle.

19. The feedstuff composition of claim 16 that is formulated for administration to turkeys.

* * * * *